United States Patent [19]
Kretz

[11] Patent Number: 6,110,719
[45] Date of Patent: Aug. 29, 2000

[54] PHYTASE

[75] Inventor: Keith Kretz, San Marcos, Calif.

[73] Assignee: Diversa Corporation, Del.

[21] Appl. No.: 09/259,214

[22] Filed: Mar. 1, 1999

Related U.S. Application Data

[62] Division of application No. 08/910,798, Aug. 13, 1997, Pat. No. 5,876,997.

[51] Int. Cl.⁷ .............................. C12N 9/16; A23K 1/165; A61K 38/46
[52] U.S. Cl. .................... 435/196; 424/442; 424/94.6
[58] Field of Search ............................ 435/196; 424/442, 424/94.6

[56] References Cited

U.S. PATENT DOCUMENTS

| | | | |
|---|---|---|---|
| 5,366,736 | 11/1994 | Edwards, Jr. ........................... | 424/442 |
| 5,436,156 | 7/1995 | Van Gorcom et al. ............... | 435/252.3 |
| 5,939,303 | 8/1999 | Cheng et al. ........................... | 435/196 |

OTHER PUBLICATIONS

Dassa, J. et al., J. Bacteriology, vol. 172, No. 9, pp. 5497–5500, Sep. 1990.

*Primary Examiner*—Ponnathapu Achutamurthy
*Assistant Examiner*—Peter P. Tung
*Attorney, Agent, or Firm*—Gray Cary Ware & Freidenrich LLP; Lisa A. Haile

[57] ABSTRACT

The invention provides a purified phytate enzyme derived from *Escherichia coli* B. The enzyme has a molecular weight of about 47.1 kilodaltons and has phytase activity (SEQ ID NO:2). The enzyme can be produced from native or recombinant host cells and can be used to aid in the digestion of phytate where desired. In particular, the phytase of the present invention can be used in animal feed.

7 Claims, 5 Drawing Sheets

```
1
ATG AAA GCG ATC TTA ATC CCA TTT TTA TCT CTT CTG ATT CCG TTA ACC CCG
Met Lys Ala Ile Leu Ile Pro Phe Leu Ser Leu Leu Ile Pro Leu Thr Pro

CAA TCT GCA TTC GCT CAG AGT GAG CCG GAG CTG AAG CTG GAA AGT GTG GTG
Gln Ser Ala Phe Ala Gln Ser Glu Pro Glu Leu Lys Leu Glu Ser Val Val

ATT GTC AGT CGT CAT GGT GTG CGT GCT CCA ACC AAG GCC ACG CAA CTG ATG
Ile Val Ser Arg His Gly Val Arg Ala Pro Thr Lys Ala Thr Gln Leu Met

CAG GAT GTC ACC CCA GAC GCA TGG CCA ACC TGG CCG GTA AAA CTG GGT TGG
Gln Asp Val Thr Pro Asp Ala Trp Pro Thr Trp Pro Val Lys Leu Gly Trp

CTG ACA CCG CGN GGT GAG CTA ATC GCC TAT CTC GGA CAT TAC CAA CGC
Leu Thr Pro Arg Gly Gly Glu Leu Ile Ala Tyr Leu Gly His Tyr Gln Arg

CAG CGT CTG GTA GCC GAC GGA TTG CTG GCG AAA AAG GGC TGC CCG CAG TCT
Gln Arg Leu Val Ala Asp Gly Leu Leu Ala Lys Lys Gly Cys Pro Gln Ser

GGT CAG GTC GCG ATT ATT GCT GAT GTC GAC GAG CGT ACC CGT AAA ACA GGC
Gly Gln Val Ala Ile Ile Ala Asp Val Asp Glu Arg Thr Arg Lys Thr Gly
```

FIG. 1A

GAA GCC TTC GCC GGG CTG GCA CCT GAC TGT GCA ATA ACC GTA CAT ACC
Glu Ala Phe Ala Gly Leu Ala Pro Asp Cys Ala Ile Thr Val His Thr

CAG GCA GAT ACG TCC AGT CCC GAT CCG TTA TTT AAT CCT CTA AAA ACT GGC
Gln Ala Asp Thr Ser Ser Pro Asp Pro Leu Phe Asn Pro Leu Lys Thr Gly

GTT TGC CAA CTG GAT AAC GCG AAC GTG ACT GAC GCG ATC CTC AGC AGG GCA
Val Cys Gln Leu Asp Asn Ala Asn Val Thr Asp Ala Ile Leu Ser Arg Ala

GGA GGG TCA ATT GCT GAC TTT ACC GGG CAT CGG CAA ACG GCG TTT CGC GAA
Gly Gly Ser Ile Ala Asp Phe Thr Gly His Arg Gln Thr Ala Phe Arg Glu

CTG GAA CGG GTG CTT AAT TTT CCG CAA TCA AAC TTG TGC CTT AAA CGT GAG
Leu Glu Arg Val Leu Asn Phe Pro Gln Ser Asn Leu Cys Leu Lys Arg Glu

AAA CAG GAC GAA AGC TGT TCA TTA ACG CAG GCA TTA CCA TCG GAA CTC AAG
Lys Gln Asp Glu Ser Cys Ser Leu Thr Gln Ala Leu Pro Ser Glu Leu Lys

GTG AGC GCC GAC AAT GTC TCA TTA ACC GGT GCG GTA AGC CTC GCA TCA ATG
Val Ser Ala Asp Asn Val Ser Leu Thr Gly Ala Val Ser Leu Ala Ser Met

*FIG. 1B*

CTG ACG GAG ATA TTT CTC CTG CAA CAA GCA CAG GGA ATG CCG GAG CCG GGG
Leu Thr Glu Ile Phe Leu Leu Gln Gln Ala Gln Gly Met Pro Glu Pro Gly

TGG GGA AGG ATC ACC GAT TCA CAC CAG TGG AAC ACC TTG CTA AGT TTG CAT
Trp Gly Arg Ile Thr Asp Ser His Gln Trp Asn Thr Leu Leu Ser Leu His

AAC GCG CAA TTT TAT TTG CTA CAA CGC ACG CCA GAG GTT GCC CGC AGC CGC
Asn Ala Gln Phe Tyr Leu Leu Gln Arg Thr Pro Glu Val Ala Arg Ser Arg

GCC ACC CCG TTA TTG GAT TTG ATC ATG GCA GCG TTG ACG CCC CAT CCA CCG
Ala Thr Pro Leu Leu Asp Leu Ile Met Ala Ala Leu Thr Pro His Pro Pro

CAA AAA CAG GCG TAT GGT GTG ACA TTA CCC ACT TCA GTA CTG TTT ATT GCC
Gln Lys Gln Ala Tyr Gly Val Thr Leu Pro Thr Ser Val Leu Phe Ile Ala

GGA CAC GAT ACT AAT CTG GCA AAT CTC GGC GGC GCA CTG GAG CTC AAC TGG
Gly His Asp Thr Asn Leu Ala Asn Leu Gly Gly Ala Leu Glu Leu Asn Trp

ACG CTT CCC GGT CAG CCG GAT AAC ACG CCG CCA GGT GAA CTG GTG TTT
Thr Leu Pro Gly Gln Pro Asp Asn Thr Pro Pro Gly Glu Leu Val Phe

*FIG. 1C*

GAA CGC TGG CGT CGG CTA AGC GAT AAC AGC CAG TGG ATT CAG GTT TCG CTG
Glu Arg Trp Arg Arg Leu Ser Asp Asn Ser Gln Trp Ile Gln Val Ser Leu

GTC TTC CAG ACT TTA CAG CAG ATG CGT GAT AAA ACG CCG CTG TCA TTA AAT
Val Phe Gln Thr Leu Gln Gln Met Arg Asp Lys Thr Pro Leu Ser Leu Asn

ACG CCC GGA GAG GTG AAA CTG ACC CTG GCA GGA TGT GAA GAG CGA AAT
Thr Pro Gly Glu Val Lys Leu Thr Leu Ala Gly Cys Glu Glu Arg Asn

GCG CAG GGC ATG TGT TCG TTG GCA GGT TTT ACG CAA ATC GTG AAT GAA GCA
Ala Gln Gly Met Cys Ser Leu Ala Gly Phe Thr Gln Ile Val Asn Glu Ala

CGC ATA CCG GCG TGC AGT TTG AGA TCT CAT CAC CAT CAC CAC TAA 1323
Arg Ile Pro Ala Cys Ser Leu Arg Ser His His His His His End

*FIG. 1D*

SEQUENCE LISTING

```
<160> NUMBER OF SEQ ID NOS: 4

<210> SEQ ID NO 1
<211> LENGTH: 1323
<212> TYPE: DNA
<213> ORGANISM: Escherichia coli
<220> FEATURE:
<221> NAME/KEY: CDS
```

```
<222> LOCATION: (1)...(1320)
<221> NAME/KEY: misc_feature
<222> LOCATION: (1)...(1323)
<223> OTHER INFORMATION: n = A,T,C or G

<400> SEQUENCE: 1 atg aaa gcg atc tta atc cca ttt tta tct ctt ctg att ccg tta acc      48
Met Lys Ala Ile Leu Ile Pro Phe Leu Ser Leu Leu Ile Pro Leu Thr
1               5                   10                  15 ccg caa tct gca ttc gct cag agt gag ccg gag ctg aag ctg gaa agt      96
Pro Gln Ser Ala Phe Ala Gln Ser Glu Pro Glu Leu Lys Leu Glu Ser
            20                  25                  30 gtg gtg att gtc agt cgt cat ggt gtg cgt gct cca acc aag gcc acg     144
Val Val Ile Val Ser Arg His Gly Val Arg Ala Pro Thr Lys Ala Thr
        35                  40                  45 caa ctg atg cag gat gtc acc cca gac gca tgg cca acc tgg ccg gta     192
Gln Leu Met Gln Asp Val Thr Pro Asp Ala Trp Pro Thr Trp Pro Val
50                  55                  60 aaa ctg ggt tgg ctg aca ccg cgn ggt ggt gag cta atc gcc tat ctc     240
Lys Leu Gly Trp Leu Thr Pro Arg Gly Gly Glu Leu Ile Ala Tyr Leu
65                  70                  75                  80 gga cat tac caa cgc cag cgt ctg gta gcc gac gga ttg ctg gcg aaa     288
Gly His Tyr Gln Arg Gln Arg Leu Val Ala Asp Gly Leu Leu Ala Lys
                85                  90                  95 aag ggc tgc ccg cag tct ggt cag gtc gcg att att gct gat gtc gac     336
Lys Gly Cys Pro Gln Ser Gly Gln Val Ala Ile Ile Ala Asp Val Asp
            100                 105                 110 gag cgt acc cgt aaa aca ggc gaa gcc ttc gcc gcc ggg ctg gca cct     384
Glu Arg Thr Arg Lys Thr Gly Glu Ala Phe Ala Ala Gly Leu Ala Pro
        115                 120                 125 gac tgt gca ata acc gta cat acc cag gca gat acg tcc agt ccc gat     432
Asp Cys Ala Ile Thr Val His Thr Gln Ala Asp Thr Ser Ser Pro Asp
130                 135                 140 ccg tta ttt aat cct cta aaa act ggc gtt tgc caa ctg gat aac gcg     480
Pro Leu Phe Asn Pro Leu Lys Thr Gly Val Cys Gln Leu Asp Asn Ala
145                 150                 155                 160 aac gtg act gac gcg atc ctc agc agg gca gga ggg tca att gct gac     528
Asn Val Thr Asp Ala Ile Leu Ser Arg Ala Gly Gly Ser Ile Ala Asp
                165                 170                 175 ttt acc ggg cat cgg caa acg gcg ttt cgc gaa ctg gaa cgg gtg ctt     576
Phe Thr Gly His Arg Gln Thr Ala Phe Arg Glu Leu Glu Arg Val Leu
            180                 185                 190 aat ttt ccg caa tca aac ttg tgc ctt aaa cgt gag aaa cag gac gaa     624
Asn Phe Pro Gln Ser Asn Leu Cys Leu Lys Arg Glu Lys Gln Asp Glu
        195                 200                 205 agc tgt tca tta acg cag gca tta cca tcg gaa ctc aag gtg agc gcc     672
Ser Cys Ser Leu Thr Gln Ala Leu Pro Ser Glu Leu Lys Val Ser Ala
210                 215                 220 gac aat gtc tca tta acc ggt gcg gta agc ctc gca tca atg ctg acg     720
Asp Asn Val Ser Leu Thr Gly Ala Val Ser Leu Ala Ser Met Leu Thr
225                 230                 235                 240 gag ata ttt ctc ctg caa caa gca cag gga atg ccg gag ccg ggg tgg     768
Glu Ile Phe Leu Leu Gln Gln Ala Gln Gly Met Pro Glu Pro Gly Trp
                245                 250                 255 gga agg atc acc gat tca cac cag tgg aac acc ttg cta agt ttg cat     816
Gly Arg Ile Thr Asp Ser His Gln Trp Asn Thr Leu Leu Ser Leu His
            260                 265                 270 aac gcg caa ttt tat ttg cta caa cgc acg cca gag gtt gcc cgc agc     864
Asn Ala Gln Phe Tyr Leu Leu Gln Arg Thr Pro Glu Val Ala Arg Ser
        275                 280                 285
```

```
cgc gcc acc ccg tta ttg gat ttg atc atg gca gcg ttg acg ccc cat    912
Arg Ala Thr Pro Leu Leu Asp Leu Ile Met Ala Ala Leu Thr Pro His
    290                 295                 300 cca ccg caa aaa cag gcg tat ggt gtg aca tta ccc act tca gta ctg    960
Pro Pro Gln Lys Gln Ala Tyr Gly Val Thr Leu Pro Thr Ser Val Leu
305                 310                 315                 320 ttt att gcc gga cac gat act aat ctg gca aat ctc ggc ggc gca ctg   1008
Phe Ile Ala Gly His Asp Thr Asn Leu Ala Asn Leu Gly Gly Ala Leu
                325                 330                 335 gag ctc aac tgg acg ctt ccc ggt cag ccg gat aac acg ccg cca ggt   1056
Glu Leu Asn Trp Thr Leu Pro Gly Gln Pro Asp Asn Thr Pro Pro Gly
            340                 345                 350 ggt gaa ctg gtg ttt gaa cgc tgg cgt cgg cta agc gat aac agc cag   1104
Gly Glu Leu Val Phe Glu Arg Trp Arg Arg Leu Ser Asp Asn Ser Gln
        355                 360                 365 tgg att cag gtt tcg ctg gtc ttc cag act tta cag cag atg cgt gat   1152
Trp Ile Gln Val Ser Leu Val Phe Gln Thr Leu Gln Gln Met Arg Asp
    370                 375                 380 aaa acg ccg ctg tca tta aat acg ccg ccc gga gag gtg aaa ctg acc   1200
Lys Thr Pro Leu Ser Leu Asn Thr Pro Pro Gly Glu Val Lys Leu Thr
385                 390                 395                 400 ctg gca gga tgt gaa gag cga aat gcg cag ggc atg tgt tcg ttg gca   1248
Leu Ala Gly Cys Glu Glu Arg Asn Ala Gln Gly Met Cys Ser Leu Ala
                405                 410                 415 ggt ttt acg caa atc gtg aat gaa gca cgc ata ccg gcg tgc agt ttg   1296
Gly Phe Thr Gln Ile Val Asn Glu Ala Arg Ile Pro Ala Cys Ser Leu
            420                 425                 430 aga tct cat cac cat cac cat cac taa                               1323
Arg Ser His His His His His His
        435                 440

<210> SEQ ID NO 2
<211> LENGTH: 440
<212> TYPE: PRT
<213> ORGANISM: Escherichia coli

<400> SEQUENCE: 2

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160
```

Asn Val Thr Asp Ala Ile Leu Ser Arg Ala Gly Gly Ser Ile Ala Asp
            165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
            195                 200                 205

Ser Cys Ser Leu Thr Gln Ala Leu Pro Ser Glu Leu Lys Val Ser Ala
            210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
                275                 280                 285

Arg Ala Thr Pro Leu Leu Asp Leu Ile Met Ala Ala Leu Thr Pro His
            290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
                355                 360                 365

Trp Ile Gln Val Ser Leu Val Phe Gln Thr Leu Gln Gln Met Arg Asp
            370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430

Arg Ser His His His His His His
            435                 440

<210> SEQ ID NO 3
<211> LENGTH: 49
<212> TYPE: DNA
<213> ORGANISM: Artificial Sequence
<220> FEATURE:
<223> OTHER INFORMATION: Oligonucleotide

<400> SEQUENCE: 3
gtttctgaat tcaaggagga atttaaatga aagcgatctt aatcccatt          49

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide

<400> SEQUENCE: 4
gtttctggat ccttacaaac tgcacgccgg tat          33

PHYTASE

This application is a Divisional of patent application Ser. No. 08/910,798, filed Aug. 13, 1997, now U.S. Pat. No. 5,876,997, issued Mar. 2, 1999.

FIELD OF THE INVENTION

This invention relates to newly identified polynucleotides, polypeptides encoded by such polynucleotides, the use of such polynucleotides and polypeptides, as well as the production and isolation of such polynucleotides and polypeptides. More particularly, the polypeptides of the present invention have been identified as phytases and in particular, enzymes having phytase activity.

BACKGROUND

Minerals are essential elements for the growth of all organisms. For livestock production of monogastric animals (e.g., pigs, poultry) and fish, feed is commonly supplemented with minerals. Plant seeds are a rich source of minerals since they contain ions that are complexed with the phosphate groups of phytic acid. Ruminants do not require inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released.

Phytate occurs as a source of stored phosphorous in virtually all plant feeds (Phytic Acid, Chemistry and Applications, E. Graf (Ed.), Pilatus Press: Minneapolis, Minn., U.S.A., 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are only partially available for absorption by monogastric animals, which lack phytase activity. Although some hydrolysis of phytate occurs in the colon, most phytate passes through the gastrointestinal tract of monogastric animals and is excreted in the manure contributing to fecal phosphate pollution problems in areas of intense livestock production. Inorganic phosphorous released in the colon has no nutritional value to livestock because inorganic phosphorous is absorbed only in the small intestine. Thus, a significant amount of the nutritionally important dietary minerals are potentially not available to monogastric animals.

Conversion of phytate to inositol and inorganic phosphorous can be catalyzed by microbial enzymes referred to broadly as phytases. Phytases such as phytase #EC 3.1.3.8 are capable of catalyzing hydrolysis of myo-inositol hexaphosphate to D-myo-inositol 1,2,4,5,6-pentaphosphate and orthophosphate. Certain fungal phytases reportedly hydrolyze inositol pentaphosphate to tetra-, tri-, and lower phosphates; e.g., *A. ficuum* phytases reportedly produce mixtures of myoinositol di- and mono-phosphate (Ullah, 1988). Phytase producing microorganisms comprise bacteria such as *Bacillus subtilis* (V. K. Powar and V. J. Jagannathan, J. Bacteriol. 151:1102–1108, 1982) and Pseudomonas (D. J. Cosgrove, Austral. J. Biol. Sci. 2:1207–1220, 1970); yeasts such as *Sacchoromyces cerevisiae* (N. R. Nayini and P. Markakis, Lebensmittel Wissenschaft und Technologie 17:24–26, 1984); and fungi such as *Aspergillus terreus* (K. Yamada, et al., Agric. Biol Chem. 32:1275–1282, 1968). The possible use of microbes capable of producing phytase as a feed additive for monogastric animals has been reported previously (Shieh and Ware, U.S. Pat. No. 3,297,548; Nelson, T. S. et al., J. Nutrition 101:1289–1294, 1971).

Microbial phytases may also reportedly be useful for producing animal feed from certain industrial processes, e.g., wheat and corn waste products. The wet milling process of corn produces glutens sold as animal feeds. Addition of phytase may reportedly improve the nutritional value of the feed product. Fungal phytase enzymes and process conditions (t~50° C. and pH ~5.5) have been reported previously in European Patent Application 0 321 004. In processing soybean meal the presence of phytate reportedly renders the meal and wastes unsuitable for feeds used in rearing fish, poultry and other non-ruminants as well as calves fed on milk. Phytase is reportedly useful for improving the nutrient and commercial value of this high protein soy material (see Finase Enzymes by Alko, Rajamaki, Finland). A combination of phytase and a pH 2.5 optimum acid phosphatase form *A. niger* has been used by Alko, Ltd as an animal feed supplement in their phytic acid degradative product Finas F and Finase S. A cost-effective source of phytase would greatly enhance the value of soybean meals as an animal feed (Shieh et al., 1969).

Phytase and less specific acid phosphatases are produced by the fungus *Aspergillus ficuum* as extracellular enzymes (Shieh et al., 1969). Ullah reportedly purified a phytase from wild-type *A. ficuum* that had an apparent molecular weight of 61.7 kDA (on SDS-PAGE; as corrected for glycosylation); pH optima at pH 2.5 and pH 5.5; a Km of about 40 $\mu$m; and, a specific activity of about 50U/mg (Ullah, A., Preparative Biochem 18:443–458, 1988); PCT patent application WO 91/05053 also reportedly discloses isolation and molecular cloning of a phytase from *Aspergillus ficuum* with pH optima at pH 2.5 and pH 5.5, a Km of about 250 $\mu$m, and specific activity of about 100U/mg protein.

Acid phosphatases are enzymes that catalytically hydrolyze a wide variety of phosphate esters and usually exhibit pH optima below 6.0 (Hollander, 1971); e.g., #EC 3.1.3.2 catalyzes hydrolysis of orthophosphoric monoesters to orthophosphate products. An acid phosphatase has reportedly been purified from *A. ficuum*. The deglycosylated form of the acid phosphatase has an apparent molecular weight of 32.6 kDa (Ullah et al., 1987).

The object of the present invention provides a recombinant phytase isolated from *Escherichia coli* B that improves the efficiency of release of phosphorous from phytate and the salts of phytic acid. Another object of the present invention provides a source of a recombinant enzyme that is suitable for commercial use in feeds and industrial processes with minimal processing.

SUMMARY OF THE INVENTION

The present invention provides a polynucleotide and a polypeptide encoded thereby which has been identified as a phytase enzyme having phytase activity. In accordance with one aspect of the present invention, there is provided a novel recombinant enzyme, as well as active fragments, analogs and derivatives thereof.

In accordance with another aspect of the present invention, there are provided isolated nucleic acid molecules encoding the enzyme of the present invention including mRNA, DNA, cDNA, genomic DNA as well as active analogs and fragments of such enzyme.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzyme, or polynucleotide encoding such enzymes for use in commercial processes, such as, for example, processes that liberate minerals from phytates in plant materials either in vitro, i.e., in feed treatment processes, or in vivo, i.e., by administering the enzyme to animals.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1D show the nucleotide and deduced amino acid sequences the enzyme of the present invention. Sequencing was performed using a 378 automated DNA sequencer (Applied Biosystems, Inc.).

DETAILED DESCRIPTION OF THE INVENTION

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The present invention provides purified a recombinant enzyme that catalyzes the hydrolysis of phytate to inositol and free phosphate with release of minerals from the phytic acid complex. An exemplary purified enzyme is a phytase derived from *Escherichia coli* B. This exemplary enzyme is shown in FIG. 1, SEQ ID NO:2.

The polynucleotide encoding SEQ ID NO:2 was originally recovered from genomic DNA isolated from *Escherichia coli* B as described below. It contains an open reading frame encoding a protein of 432 amino acid residues.

Figure 2B:
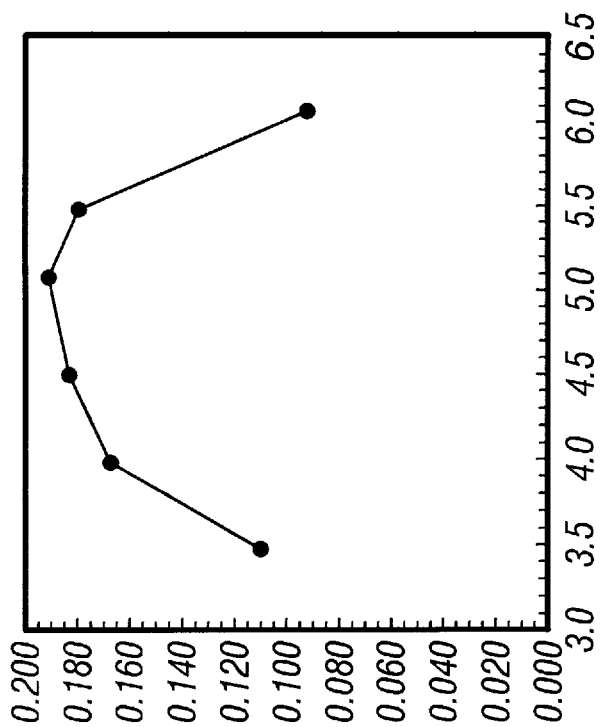
FIGS. 2A and B show the pH and temperature profile and stability data for the phytase enzyme of the present invention. The assay used for these analysis is the following for the detection of phytase activity: Phytase activity is measured by incubating 150 μl of the enzyme preparation with 600 μl of 2 mM sodium phytate in 100 mM Tris HCl buffer pH 7.5, supplemented with 1 mM $CaCl_2$ for 30 minutes at 37° C. After incubation the reaction is stopped by adding 750 μl of 5% trichloroacetic acid. Phosphate released was measured against phosphate standard spectrophotometrically at 700 nm after adding 1500° 1 of the color reagent (4 volumes of 1.5% ammonium molybdate in 5.5% sulfuric acid and 1 volume of 2.7% ferrous sulfate; Shimizu, M., 1992; Biosci. Biotech. Biochem., 56:1266–1269). OD at 700 nm is indicated on the Y-axis of the graphs in FIG. 2. Temperature or pH is indicated on the X-axis of the graphs.
Figure 2A:
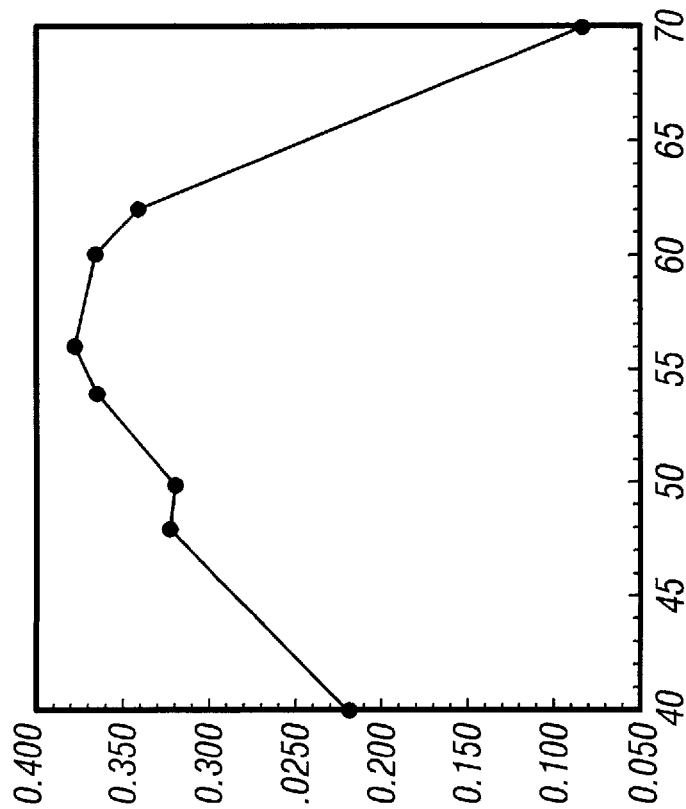

In one embodiment, the phytase enzyme of SEQ ID NO:2 of the present invention has a molecular weight of about 47,056 kilodaltons as measured by SDS-PAGE gel electrophoresis and an inferred molecular weight from the nucleotide sequence of the gene. The pI is 6.70. The pH and temperature profile and stability data for this enzyme is presented in FIG. 2. This purified enzyme may be used to catalyze the hydrolysis of phytate to inositol and free phosphate where desired. The phytase enzyme of the present invention has a high thermostability.

In accordance with an aspect of the present invention, there are provided isolated nucleic acid molecules polynucleotides) which encode for the mature enzyme having the deduced amino acid sequence of FIG. 1.

This invention can be used to isolate nucleic acid sequences substantially similar to the isolated nucleic acid molecule encoding an phytase enzyme disclosed in FIG. 1 (SEQ ID NO:1),. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1. Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding a phytase enzyme is to probe a genomic gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately $2\times10^7$ cpm (specific activity $4-9\times10^8$ cpm/ug) of $^{32}P$ end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The present invention provides a substantially pure phytase enzyme. The term "substantially pure" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The phytase polypeptide included in the invention can have the amino acid sequences of Phytase shown in FIG. 1 (SEQ ID NO:1). Phytase polypeptides, such as those isolated from E. coli B, can be characterized by catalyzing the hydrolysis of phytate to inositol and free phosphate with the release of minerals from the phytic acid complex.

Also included in the invention are polypeptides having sequences that are "substantially identical" to the sequence of a phytase polypeptide, such as one of SEQ ID 1. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Fragments of the phytase polypeptide of the present invention can retain at least one phytase-specific activity or epitope. Phytase activity can be assayed by examining the catalysis of phytate to inositol and free phosphate. For example, a phytase polypeptide fragment containing, e.g., at least 8–10 amino acids can be used as an immunogen in the production of phytase-specific antibodies. The fragment can contain, for example, an amino acid sequence that is conserved in phytases, and this amino acid sequence can contain amino acids that are conserved in phytases. Such fragments can easily be identified by comparing the sequences of phytases found in FIG. 1. In addition to their use as peptide immunogens, the above-described phytase fragments can be used in immunoassays, such as ELISAs, to detect the presence of phytase-specific antibodies in samples.

The phytase polypeptide of the invention can be obtained using any of several standard methods. For example, phytase polypeptides can be produced in a standard recombinant expression systems (see below), chemically synthesized (this approach may be limited to small phytase peptide fragments), or purified from organisms in which they are naturally expressed.

The invention also provides isolated nucleic acid molecules that encode the phytase polypeptide described above. For example, nucleic acids that encode SEQ ID NO:1 are included in the invention. These nucleic acids can contain naturally occurring nucleotide sequences, or sequences that differ from those of the naturally occurring nucleic acids that encode phytases, but encode the same amino acids, due to the degeneracy of the genetic code. The nucleic acids of the invention can contain DNA or RNA nucleotides, or combinations or modifications thereof. Exemplary nucleic acids of the invention are shown in SEQ ID NO:1.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived.

The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The nucleic acid molecules of the invention can be used as templates in standard methods for production of phytase gene products (e.g., phytase RNAs and phytase polypeptides ). In addition, the nucleic acid molecules that encode phytase polypeptides (and fragments thereof) and related nucleic acids, such as (1) nucleic acids containing sequences that are complementary to, or that hybridize to, nucleic acids encoding phytase polypeptides, or fragments thereof (e.g., fragments containing at least 12, 15, 20, or 25 nucleotides); and (2) nucleic acids containing sequences that hybridize to sequences that are complementary to nucleic acids encoding phytase polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing phytase nucleic acids, methods for detecting the presence of a phytase nucleic acid in a sample, screening methods for identifying nucleic acids encoding new phytase family members.

The invention also includes methods for identifying nucleic acid molecules that encode members of the phytase polypeptide family in addition to SEQ ID NO:1. In these methods, a sample, e.g., a nucleic acid library, such as a cDNA library, that contains a nucleic acid encoding a phytase polypeptide is screened with a phytase-specific probe, e.g., a phytase-specific nucleic acid probe. Phytase-specific nucleic acid probes are nucleic acid molecules (e.g., molecules containing DNA or RNA nucleotides, or combinations or modifications thereof) that specifically hybridize to nucleic acids encoding phytase polypeptides, or to complementary sequences thereof. The term "phytase-specific probe," in the context of this method of invention, refers to probes that bind to nucleic acids encoding phytase polypeptides, or to complementary sequences thereof, to a detectably greater extent than to nucleic acids encoding other enzymes, or to complementary sequences thereof.

The invention facilitates production of phytase-specific nucleic acid probes. Methods for obtaining such probes can be designed based on the amino acid sequences shown in FIG. 1. The probes, which can contain at least 12, e.g., at least 15, 25, 35, 50, 100, or 150 nucleotides, can be produced using any of several standard methods (see, e.g., Ausubel, et al, supra). For example, preferably, the probes are generated using PCR amplification methods. In these methods, primers are designed that correspond to phytase-conserved sequences (see FIG. 1), which can include phytase-specific amino acids, and the resulting PCR product is used as a probe to screen a nucleic acid library, such as a cDNA library.

The deposit has been made under the terms of the Budapest Treaty on the International Recognition of the deposit of micro-organisms for purposes of patent procedure. The DNA will be irrevocably and without restriction or condition released to the public upon the issuance of a patent. The deposit is provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

The coding sequences for the phytase enzymes of the present invention were identified by preparing E. coli B genomic DNA, for example, and recovering (via, for example, PCR amplification) from the genomic DNA, DNA encoding phytase activity. Such methods for recovery are well-known in the art. One means, for example, comprises designing amplification primers to recover the coding sequence, amplifying the gene from the genomic DNA, subcloning the DNA into a vector, transforming the resulting construct into a host strain, and expressing the phytase enzyme for evaluation. Such procedures are well known in the art and methods are provided, for example, in Maniatis, T., et al., *Molecular Cloning,* Cold Spring Harbor Press, New York, 1982, which is hereby incorporated by reference in its entirety.

In a preferred embodiment, the enzyme of the present invention, was isolated from an E. coli B genomic DNA by the following technique:
E. coli B genomic DNA was obtained from Sigma (Catalog # D-2001), St. Louis, N.J. The following primers were used to amplify the gene directly from the genomic DNA:

5' primer gtttctgaattcaaggaggaatttaaAT-
GAAAGCGATCTTAATCCCATT (SEQ ID NO:3)

3' primer gtttctggatccTTACAAACTGCACGCCGGTAT (SEQ ID NO:4)

Pfu polymerase was used according to manufacturers protocol (Stratagene Cloning Systems, Inc., La Jolla, Calif.). PCR product and pQE60 vector (Qiagen) were both digested with EcoRI and BglII restriction endonucleases (New England Biolabs) according to manufacturers protocols. Ligation and transformation into, and expression in M15 pREP4 host cells (Qiagen) yields c-term 6X-His tagged protein.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated nucleic acid sequences and other enzymes may then be measured for retention of biological activity characteristic to the enzyme of the present invention, for example, in an assay for detecting enzymatic phytase activity. Such enzymes include truncated forms of phytase, and variants such as deletion and insertion variants.

Examples of such assays include the following assay for the detection of phytase activity:

Phytase activity can be measured by incubating 150 μl of the enzyme preparation with 600 μl of 2 mM sodium phytate in 100 mM Tris HCl buffer pH 7.5, supplemented with 1 mM CaCl$_2$ for 30 minutes at 37° C. After incubation the reaction is stopped by adding 750 µl of 5% trichloroacetic acid. Phosphate released was measured against phosphate standard spectrophotometrically at 700 nm after adding 1500 µl of the color reagent (4 volumes of 1.5% ammonium molybdate in 5.5% sulfuric acid and 1 volume of 2.7% ferrous sulfate; Shimizu, M., 1992; Biosci. Biotech. Biochem., 56:1266–1269). One unit of enzyme activity is defined as the amount of enzyme required to liberate one (mol Pi per min under assay conditions. Specific activity can be expressed in units of enzyme activity per mg of protein.

The enzyme of the present invention has enzymatic activity with respect to the hydrolysis of phytate to inositol and free phosphate.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequences shown in FIG. 1 and/or that of the deposited clone (SEQ ID NO:1), or may be a different coding sequence which coding sequence, as a result of the redundancy or degeneracy of the genetic code, encodes the same mature enzyme as the DNA of FIG. 1 (e.g., SEQ ID NO:1).

The polynucleotide which encodes for the mature enzyme of FIG. 1 (e.g., SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for analogs and derivatives of the enzyme having the deduced amino acid sequence of FIG. 1 (e.g., SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 as well as variants of such polynucleotides which variants encode for a derivative or analog of the enzyme of FIG. 1. Such nucleotide variants include deletion variants, substitution variants and addition or insertion variants.

As hereinabove indicated, the polynucleotide may have a coding sequence which is a naturally occurring allelic variant of the coding sequence shown in FIG. 1. As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

The present invention further relates to a enzyme which has the deduced amino acid sequence of FIG. 1, as well as analogs and derivatives of such enzyme.

The terms "derivative" and "analog" when referring to the enzyme of FIG. 1 means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The derivative or analog of the enzyme of FIG. 1 may be (i) one in which one or more of the amino acid residues are substituted with an amino acid residue which is not encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention includes an enzyme of FIG. 1 (in particular the mature enzyme).

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

A variant, i.e. a "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), Å-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzyme of this invention may be employed for any purpose in which such enzyme activity is necessary or desired. In a preferred embodiment the enzyme is employed for catalyzing the hydrolysis of phytate. The degradation of phytate may be used in animal feed.

In a preferred embodiment, the enzyme of the present invention is a phytase enzyme which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of 50° C. optimum above 50° C.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

The term "antibody," as used herein, refers to intact immunoglobulin molecules, as well as fragments of immunoglobulin molecules, such as Fab, Fab', (Fab')$_2$, Fv, and SCA fragments, that are capable of binding to an epitope of an endoglucanase polypeptide. These antibody fragments, which retain some ability to selectively bind to the antigen (e.g., an endoglucanase antigen) of the antibody from which they are derived, can be made using well known methods in the art (see, e.g., Harlow and Lane, supra), and are described further, as follows.

(1) A Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) A (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing phytase-specific antibodies include phytase polypeptides, e.g., any of the phytase shown in FIG. 1 polypeptide fragments. The polypeptide or peptide used to immunize an animal can be obtained by standard recombinant, chemical synthetic, or purification methods.

As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Phytase-specific polyclonal and monoclonal antibodies can be purified, for example, by binding to, and elution from, a matrix containing a phytase polypeptide, e.g., the phytase polypeptide (or fragment thereof) to which the antibodies were raised. Additional methods for antibody purification and concentration are well known in the art and can be practiced with the phytase-specific antibodies of the invention (see, for example, C oligan, et al., Unit 9, *Current Protocols in Immunology*, Wiley Interscience, 1994).

Anti-idiotype antibodies corresponding to phytase-specific antigens are also included in the invention, and can be produced using standard methods. These antibodies are raised to phytase-specific antibodies, and thus mimic phytase-specific epitopes.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

The present invention is further described with reference to the following examples; however, it is to be understood that the present invention is not limited to such examples. All parts or amounts, unless otherwise specified, are by weight.

In one aspect of the invention, a method for producing an phytase enzyme, such as those shown in FIGS. 1, is provided. The method includes growing a host cell which contains a polynucleotide encoding the enzyme (e.g., SEQ ID NO:1), under conditions which allow the expression of the nucleic acid, and isolating the enzyme encoded by the nucleic acid. Methods of culturing the host cell are described in the Examples and are known by those of skill in the art.

In another embodiment, the invention provides a method for catalyzing the hydrolysis of phytate to inositol and free phosphate with release of minerals from the phytic acid complex. The method includes contacting phytate with a degrading effective amount of an enzyme of the invention, such as the enzyme shown in SEQ ID NO:1. The term "degrading effective" amount refers to the amount of enzyme which is required to degrade at least 50% of the phytate, as compared to phytate not contacted with the enzyme. Preferably, at least 80% of the phytate is degraded.

In another embodiment, the invention provides a method for hydrolyzing phospho-mono-ester bonds in phosphate, the method including administering an effective amount of an enzyme of the invention (e.g., SEQ ID NO:1), to yield inositol and free phosphate. An "effective" amount refers to the amount of enzyme which is required to hydrolyze at least 50% of the phospho-mono-ester bonds, as compared to phytate not contacted with the enzyme. Preferably, at least 80% of the bonds are hydrolyzed.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 ög of plasmid or DNA fragment is used with about 2 units of enzyme in about 20 öl of buffer solution. For the purpose of isolating DNA fragments for plasmid construction, typically 5 to 50 ög of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is generally performed using 8 percent polyacrylamide gel described by Goeddel, D. et al., Nucleic Acids Res., 8:4057 (1980), for example.

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Sambrook, Fritsch and Maniatus, 1989. The following examples are intended to illustrate, but not to limit, the invention. While the procedures described in the examples are typical of those that can be used to carry out certain aspects of the invention, other procedures known to those skilled in the art can also be used. The following materials and methods were used in carrying out the experiments described in the examples.

EXAMPLE 1

Isolation, Bacterial Expression and Purification of Phytase

E. coli B genomic DNA was obtained from Sigma (Catalog #D-2001), St. Louis, N.J.

The following primers were used to PCR amplify the gene directly from the genomic DNA:

5' primer gtttctgaattcaaggaggaatttaaAT-GAAAGCGATCTTAATCCCATT (SEQ ID NO:3)

3' primer gtttctggatccTTACAAACTGCACGCCGGTAT (SEQ ID NO:4)

Pfu polymerase in the PCR reaction, and amplification was performed according to manufacturers protocol (Stratagene Cloning Systems, Inc., La Jolla, Calif.).

PCR product was purified and purified product and pQE60 vector (Qiagen) were both digested with EcoRI and BglII restriction endonucleases (New England Biolabs) according to manufacturers protocols. Overnight ligations were performed using standard protocols to yield pQE60.

The amplified sequences were inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance (Kan'). Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

What is claimed is:

1. Substantially pure phytase having an amino acid sequence as set forth in SEQ ID NO:2.

2. The phytase of claim 1, wherein the phytase is encoded by SEQ ID NO:1.

3. A phytase of claim 1, wherein said amino acid sequence is encoded by a nucleic acid sequence 90 percent identical to the sequence set forth in SEQ ID NO:1.

4. A phytase of claim 1, wherein said amino acid sequence is encoded by a nucleic acid sequence 95 percent identical to the sequence set forth in SEQ ID NO:1.

5. A phytase of claim 1, wherein said amino acid sequence is encoded by a nucleic acid sequence 97 percent identical to the sequence set forth in SEQ ID NO:1.

6. An animal feed composition comprising a microbial phytase having an amino acid sequence as set forth in SEQ ID NO:2.

7. An animal feed composition comprising a microbial phytase encoded by the polynucleotide of SEQ ID NO:1.

* * * * *

UNITED STATES PATENT AND TRADEMARK OFFICE
CERTIFICATE OF CORRECTION

PATENT NO.      : 6,110,719                                            Page 1 of 1
DATED           : August 29, 2000
INVENTOR(S)     : Keith Kretz It is certified that error appears in the above-identified patent and that said Letters Patent is hereby corrected as shown below:

<u>Title page,</u>
Item [56], References Cited, OTHER PUBLICATIONS, please insert -- Greiner et al, Archives of Biochemistry and Biophysics, Vol. 303, No. 1, pp. 107-113, May 15, 1993. --

Signed and Sealed this

Twenty-ninth Day of October, 2002

*Attest:*

*Attesting Officer*

JAMES E. ROGAN
*Director of the United States Patent and Trademark Office*

UNITED STATES PATENT AND TRADEMARK OFFICE
Certificate

Patent No. 6,110,719                          Patented: August 29, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jay M. Short, Del Mar, CA.

Signed and Sealed this Twenty-fifth Day of November 2008.

NASHAAT T. NASHED
*Supervisory Patent Examiner*
Art Unit 1652